(12) United States Patent
Ross et al.

(10) Patent No.: US 6,358,260 B1
(45) Date of Patent: *Mar. 19, 2002

(54) AUTOMATIC CORNEAL SHAPER WITH TWO SEPARATE DRIVE MECHANISMS

(75) Inventors: Rod Ross, Laguna Niguel; Greggory Hughes, Fountain Valley, both of CA (US)

(73) Assignee: Med-Logics, Inc., Laguna Niguel, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 111 days.

(21) Appl. No.: 09/063,151

(22) Filed: Apr. 20, 1998

(51) Int. Cl.[7] .................................................. A61F 9/00
(52) U.S. Cl. ....................................................... 606/166
(58) Field of Search ................................. 606/166, 107

(56) References Cited

U.S. PATENT DOCUMENTS

| | | |
|---|---|---|
| 3,583,403 A | 6/1907 | Pohl et al. |
| 2,480,737 A | 8/1949 | Jayle |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,561,429 A | 2/1971 | Jewett |
| 3,624,821 A | 11/1971 | Henderson |
| 3,693,613 A | 9/1972 | Kelman |
| 3,752,161 A | 8/1973 | Bent |
| 3,763,862 A | 10/1973 | Spieth |
| 3,815,604 A | 6/1974 | O'Malley et al. |
| 3,842,839 A | 10/1974 | Malis et al. |
| 3,884,238 A | 5/1975 | O'Malley et al. |
| 3,899,829 A | 8/1975 | Storm et al. |
| 3,903,881 A | 9/1975 | Weigl |
| 3,913,584 A | 10/1975 | Walchle et al. |
| 3,920,014 A | 11/1975 | Banko |
| 3,930,505 A | 1/1976 | Wallach |
| 3,977,425 A | 8/1976 | Hayashida |
| 3,982,539 A | 9/1976 | Muriot |
| 3,986,512 A | 10/1976 | Walliser |
| 4,004,590 A | 1/1977 | Muriot |
| 4,011,869 A | 3/1977 | Seiler, Jr. |
| 4,043,342 A | 8/1977 | Morrison, Jr. |
| 4,108,182 A | 8/1978 | Hartman et al. |
| 4,135,515 A | 1/1979 | Muriot |
| 4,137,920 A | 2/1979 | Bonnet |
| 4,168,707 A | 9/1979 | Douvas et al. |
| 4,173,980 A | 11/1979 | Curtin |
| 4,178,707 A | 12/1979 | Littlefield |
| 4,204,328 A | 5/1980 | Kutner |
| 4,205,682 A | 6/1980 | Crock et al. |
| 4,210,146 A | 7/1980 | Banko |

(List continued on next page.)

OTHER PUBLICATIONS

Steinway Instrument Company, Inc., The Steinway/Barraquer In–Situ Microkeratome Set.

Primary Examiner—David O. Reip
Assistant Examiner—Vy Q. Bui
(74) Attorney, Agent, or Firm—Irell & Manella LLP

(57) ABSTRACT

A medical device that can be used to cut a cornea. The device includes a blade that is located within an opening of a ring. The ring can be placed onto a cornea. The device may further have a first drive mechanism that moves the blade in a first direction and a separate second drive mechanism that moves the blade in a second direction. The first drive mechanism may be controlled by a first input device. The second drive mechanism may be controlled by a second input device. The separate input devices and drive mechanisms may allow a surgeon to vary the shape and size of the corneal cut.

15 Claims, 5 Drawing Sheets

U.S. PATENT DOCUMENTS

| | | |
|---|---|---|
| 4,217,993 A | 8/1980 | Jess et al. |
| 4,223,676 A | 9/1980 | Wuchinich et al. |
| 4,245,815 A | 1/1981 | Willis |
| 4,246,902 A | 1/1981 | Martinez |
| 4,274,411 A | 6/1981 | Dotson, Jr. |
| 4,301,802 A | 11/1981 | Poler |
| 4,308,385 A | 12/1981 | Goorden |
| 4,308,835 A | 1/1982 | Abbey |
| 4,314,560 A | 2/1982 | Helfgott et al. |
| 4,320,761 A | 3/1982 | Haddad |
| 4,354,838 A | 10/1982 | Hoyer et al. |
| 4,395,258 A | 7/1983 | Wang et al. |
| 4,396,386 A | 8/1983 | Kurtz et al. |
| 4,428,748 A | 1/1984 | Peyman et al. |
| 4,429,696 A | 2/1984 | Hanna |
| 4,445,517 A | 5/1984 | Feild |
| 4,474,411 A | 10/1984 | Peters et al. |
| 4,475,904 A | 10/1984 | Wang |
| 4,476,862 A | 10/1984 | Pao |
| 4,481,948 A | 11/1984 | Sole |
| 4,493,695 A | 1/1985 | Cook |
| 4,493,698 A | 1/1985 | Wang et al. |
| 4,522,371 A | 6/1985 | Fox et al. |
| 4,523,911 A | 6/1985 | Braetsch et al. |
| 4,524,948 A | 6/1985 | Hall |
| 4,530,357 A | 7/1985 | Pawloski et al. |
| 4,531,934 A | 7/1985 | Kossovsky et al. |
| 4,540,406 A | 9/1985 | Miles |
| 4,555,645 A | 11/1985 | Atkinson |
| 4,589,414 A | 5/1986 | Yoshida et al. |
| 4,598,729 A | 7/1986 | Naito et al. |
| 4,660,556 A | 4/1987 | Swinger et al. |
| 4,662,370 A * | 5/1987 | Hoffmann et al. ........... 128/305 |
| 4,665,914 A | 5/1987 | Tanne |
| 4,674,499 A | 6/1987 | Pao |
| 4,674,503 A | 6/1987 | Peyman et al. |
| 4,668,570 A | 8/1987 | Kramer et al. |
| 4,690,099 A | 9/1987 | Gregan et al. |
| 4,706,687 A | 11/1987 | Rogers |
| 4,723,545 A | 2/1988 | Nixon et al. |
| 4,743,770 A | 5/1988 | Lee |
| 4,757,814 A | 7/1988 | Wang et al. |
| 4,767,403 A | 8/1988 | Hodge |
| 4,768,506 A | 9/1988 | Parker et al. |
| 4,770,654 A | 9/1988 | Rogers et al. |
| 4,782,239 A | 11/1988 | Hirose et al. |
| 4,782,849 A | 11/1988 | Hodge |
| 4,791,934 A | 12/1988 | Brunnett |
| 4,805,616 A | 2/1989 | Pao |
| 4,807,623 A | 2/1989 | Lieberman |
| 4,819,635 A | 4/1989 | Shapiro |
| 4,825,091 A | 4/1989 | Breyer et al. |
| 4,828,306 A | 5/1989 | Blatt |
| 4,830,047 A | 5/1989 | Hodge |
| 4,837,857 A | 6/1989 | Scheller et al. |
| 4,838,281 A | 6/1989 | Rogers et al. |
| 4,865,033 A | 9/1989 | Krumeich et al. |
| 4,884,570 A | 12/1989 | Krumeich et al. |
| 4,886,085 A | 12/1989 | Miller |
| 4,903,695 A | 2/1990 | Warner et al. |
| 4,909,815 A | 3/1990 | Meyer |
| 4,943,289 A | 7/1990 | Goode et al. |
| 4,965,417 A | 10/1990 | Massie |
| 4,988,347 A | 1/1991 | Goode et al. |
| 4,997,437 A | 3/1991 | Grieshaber |
| 5,011,482 A | 4/1991 | Goode et al. |
| 5,013,310 A | 5/1991 | Goode et al. |
| 5,019,076 A | 5/1991 | Yamanashi et al. |
| 5,059,204 A | 10/1991 | Lawson et al. |
| 5,083,558 A | 1/1992 | Thomas et al. |
| 5,106,364 A | 4/1992 | Hayafuji et al. |
| 5,133,713 A | 7/1992 | Huang et al. |
| 5,133,726 A | 7/1992 | Ruiz et al. |
| 5,176,628 A | 1/1993 | Charles et al. |
| 5,201,749 A | 4/1993 | Sachse et al. |
| 5,207,683 A | 5/1993 | Goode et al. |
| 5,215,104 A | 6/1993 | Steinert |
| 5,217,459 A | 6/1993 | Kamerling |
| 5,226,910 A | 7/1993 | Kajiyama et al. |
| 5,242,404 A | 9/1993 | Conley et al. |
| 5,271,379 A | 12/1993 | Phan et al. |
| 5,273,406 A | 12/1993 | Feygin |
| 5,273,524 A | 12/1993 | Fox et al. |
| 5,285,795 A | 2/1994 | Ryan et al. |
| 5,322,505 A | 6/1994 | Krause et al. |
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |
| 5,531,744 A | 7/1996 | Nardella et al. |
| 5,556,397 A | 9/1996 | Long et al. |
| 5,566,681 A | 10/1996 | Manwaring et al. |
| 35,421 A | 1/1997 | Ruiz et al. |
| D377,524 S | 1/1997 | Lipp |
| 5,611,799 A | 3/1997 | Smith |
| 5,624,394 A | 4/1997 | Barnitz et al. |
| 5,643,304 A | 7/1997 | Schechter et al. |
| 5,693,013 A | 12/1997 | Geuder |
| 5,700,240 A | 12/1997 | Barwick, Jr. et al. |
| 5,704,927 A | 1/1998 | Gillette et al. |
| 5,738,677 A | 4/1998 | Colvard et al. |
| 5,782,849 A | 7/1998 | Miller |
| 5,787,760 A | 8/1998 | Thorlakson |
| 5,795,328 A | 8/1998 | Barnitz et al. |
| 5,810,857 A | 9/1998 | Mackool |
| 5,814,010 A | 9/1998 | Ziegler |
| 5,817,075 A | 10/1998 | Giungo |
| 5,868,728 A | 2/1999 | Giungo et al. |
| 5,916,330 A | 6/1999 | Jacobson |
| 5,941,250 A | 8/1999 | Aramant et al. |
| 5,944,731 A * | 8/1999 | Hanna ........................ 606/166 |
| 5,957,921 A | 9/1999 | Mirhashemi et al. |
| 5,989,272 A | 11/1999 | Barron et al. |
| 6,013,049 A | 1/2000 | Rockley et al. |
| 6,019,754 A | 2/2000 | Kawesch |
| 6,045,563 A | 4/2000 | Duprat |
| 6,051,009 A | 4/2000 | Hellenkamp et al. |
| 6,059,805 A | 5/2000 | Sugimura et al. |
| 6,083,236 A | 7/2000 | Feingold |
| 6,086,544 A | 7/2000 | Hibner et al. |
| 6,165,189 A | 12/2000 | Ziemer |

\* cited by examiner

AUTOMATIC CORNEAL SHAPER WITH TWO SEPARATE DRIVE MECHANISMS

BACKGROUND OF THE INVENTION

1. Field of the Invention

The present invention relates to a medical device for cutting a cornea.

2. Background Information

There have been developed a number of different surgical techniques to correct hyperopic or myopic conditions of a human eye. U.S. Pat. No. 4,840,175 issued to Peyman discloses a procedure wherein a thin layer of corneal tissue is cut and removed from a cornea. A laser beam is then directed onto the exposed corneal tissue in a predetermined pattern. The laser beam ablates corneal tissue and changes the curvature of the eye.

U.S. Pat. No. 5,135,726 issued to Ruiz et al. discloses a device for cutting the cornea to expose an underlying surface for laser ablation. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while sliding the blade across the eye in a second transverse direction. The result is a flap of the cornea. The cut portion can be pulled back to expose an underlying surface.

The drive mechanism disclosed in the Ruiz patent includes a gear assembly which moves the blade across the eye in the first direction. The Ruiz device also contains an eccentric pin which is rotated to slide the blade across the cornea in the second direction. The gear assembly and the eccentric pin are both driven by a single motor.

Once the device is assembled the relative movement of the blade in the first and second directions and the corresponding shape of the corneal cut is fixed. The radius and shape of the cut cannot be varied without changing the gear assembly of the device. It would be desirable to provide a microkeratome that would readily allow a surgeon to change the shape and/or size of the cut.

It has been found that during a microkeratome procedure an eye lash may enter the gear assembly and prevent further movement of the blade. Such an event may require the surgeon to remove the blade during an intermittent point in the cut and complicate the procedure. It would therefore also be desirable to provide a microkeratome that was less susceptible to jamming than microkeratomes of the prior art.

SUMMARY OF THE INVENTION

One embodiment of the present invention is a medical device that can be used to cut a cornea. The device includes a blade that is located within an opening of a ring. The ring can be placed onto a cornea. The device may further have a first drive mechanism that moves the blade in a first direction and a separate second drive mechanism that moves the blade in a second direction.

DETAILED DESCRIPTION OF THE INVENTION

Figure 1:
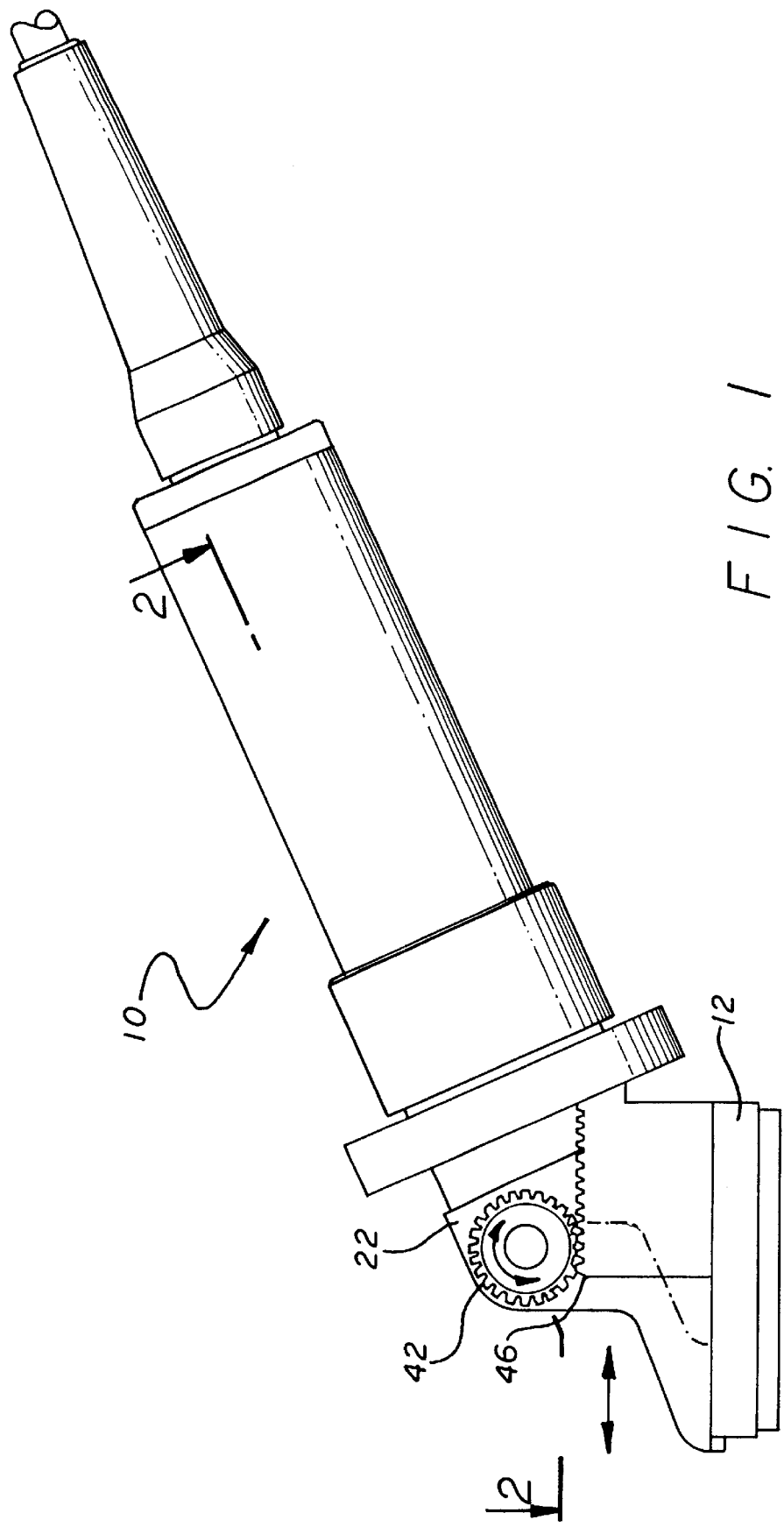
FIG. 1 is a side view of an embodiment of a medical device of the present invention.

One embodiment of the present invention is a medical device that can be used to cut a cornea. The device includes a blade that is located within an opening of a ring. The ring can be placed onto a cornea. The device may further have a first drive mechanism that moves the blade in a first direction and a separate second drive mechanism that moves the blade in a second direction.

The first drive mechanism may be controlled by a first input device. The second drive mechanism may be controlled by a second input device. The separate input devices and drive mechanisms may allow a surgeon to vary the shape and size of the corneal cut. Additionally, the first drive mechanism may cooperate with a rack that is fixed to the ring to provide movement of the blade in the first direction. The rack may be located on a pedestal that is elevated from the ring away from the eye. The elevated rack is less susceptible to the inclusion of an eye lash during the operation of the device.

Referring to the drawings more particularly by reference numbers, FIGS. 1–5 show an embodiment of a medical device 10 of the present invention. The device 10 may include a ring 12 that is placed onto a cornea (not shown). The ring 12 may have a port 14 which is coupled to a vacuum source (not shown). The vacuum source may create a vacuum pressure that pulls the ring 12 onto the cornea. The vacuum pressure prevents the ring 12 from moving during a procedure.

The device 10 may have a blade 16 that is located within an opening 18 of the ring 12. The blade 16 can move within the opening 18 in a first direction and a second transverse direction. The simultaneous movement of the blade 16 can create a radial cut across the surface of the eye. The device 10 may include a plate 19 that is mounted to the ring 12 and which flattens the cornea.

Figure 5:
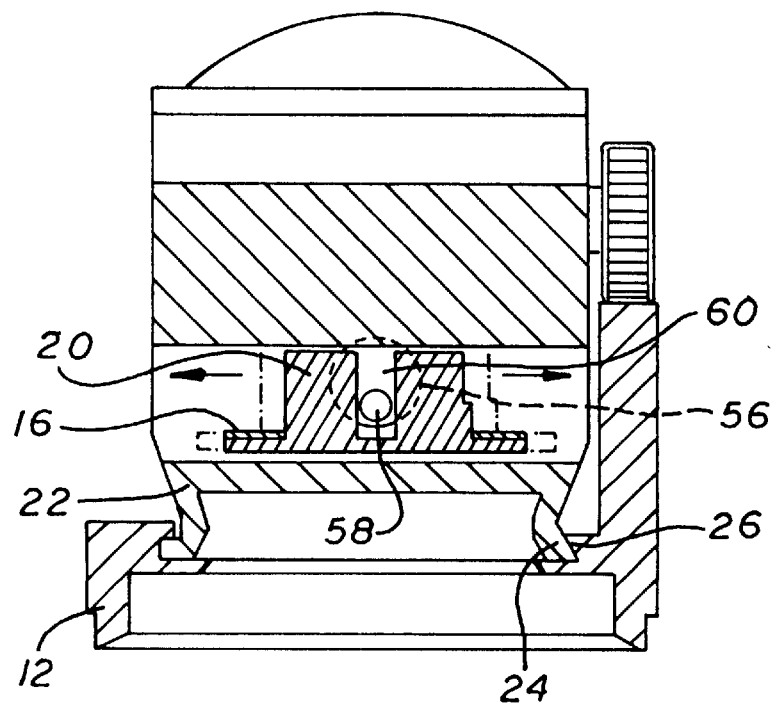
FIG. 5 is a cross-sectional view taken at line 5—5 of FIG. 3.

The blade 16 is attached to a blade holder 20. The blade holder 20 is attached to a head 22. The head 22 and blade holder 20 both move with the blade 16 relative to the ring 12. The blade holder 20 moves in the second direction while being pulled in the first direction. The head 22 only moves in the first direction. As shown in FIG. 5, each lower edge of the head 22 may have a dovetail shape 24 which cooperates a similar shaped slot 26 in the ring 12. The dovetail shape 24 and slot 26 prevent movement of the head 22 in the second direction while allowing movement in the first direction.

Figure 2:
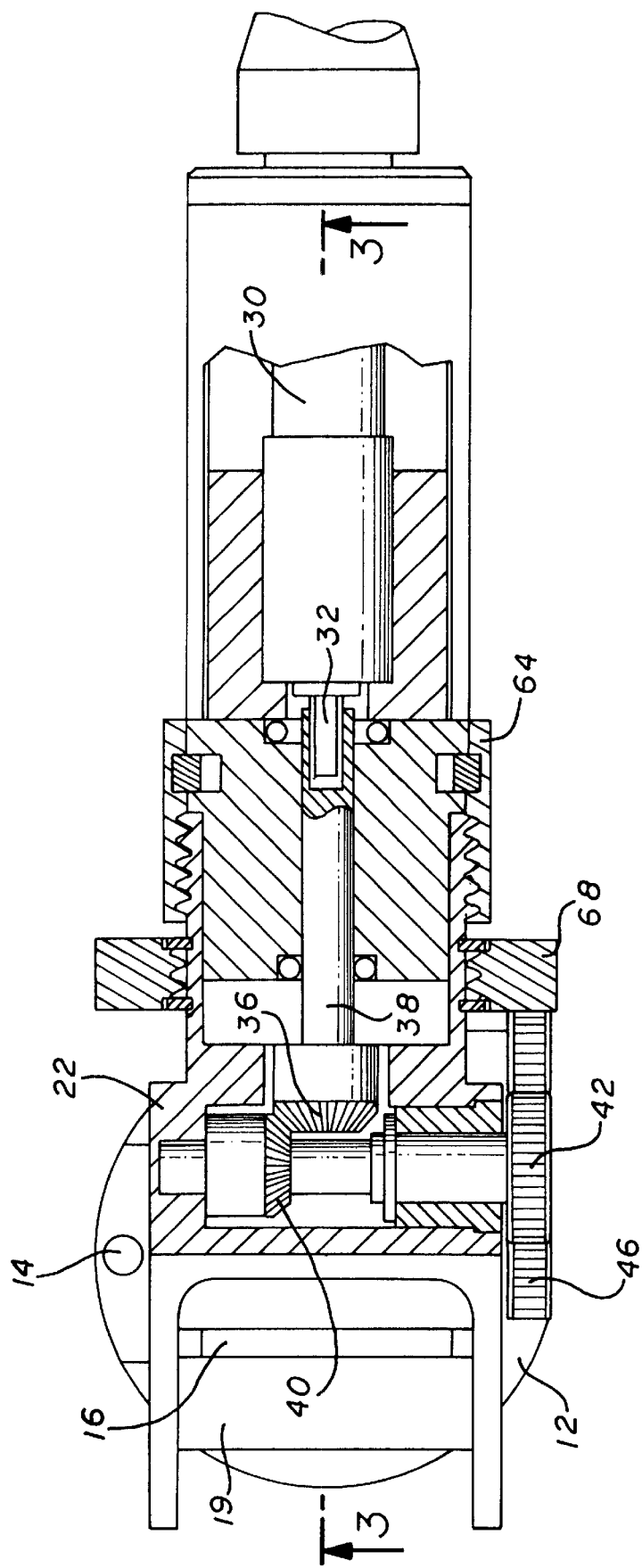
FIG. 2 is a cross-sectional view taken at line 2—2 of FIG. 1.
Figure 3:
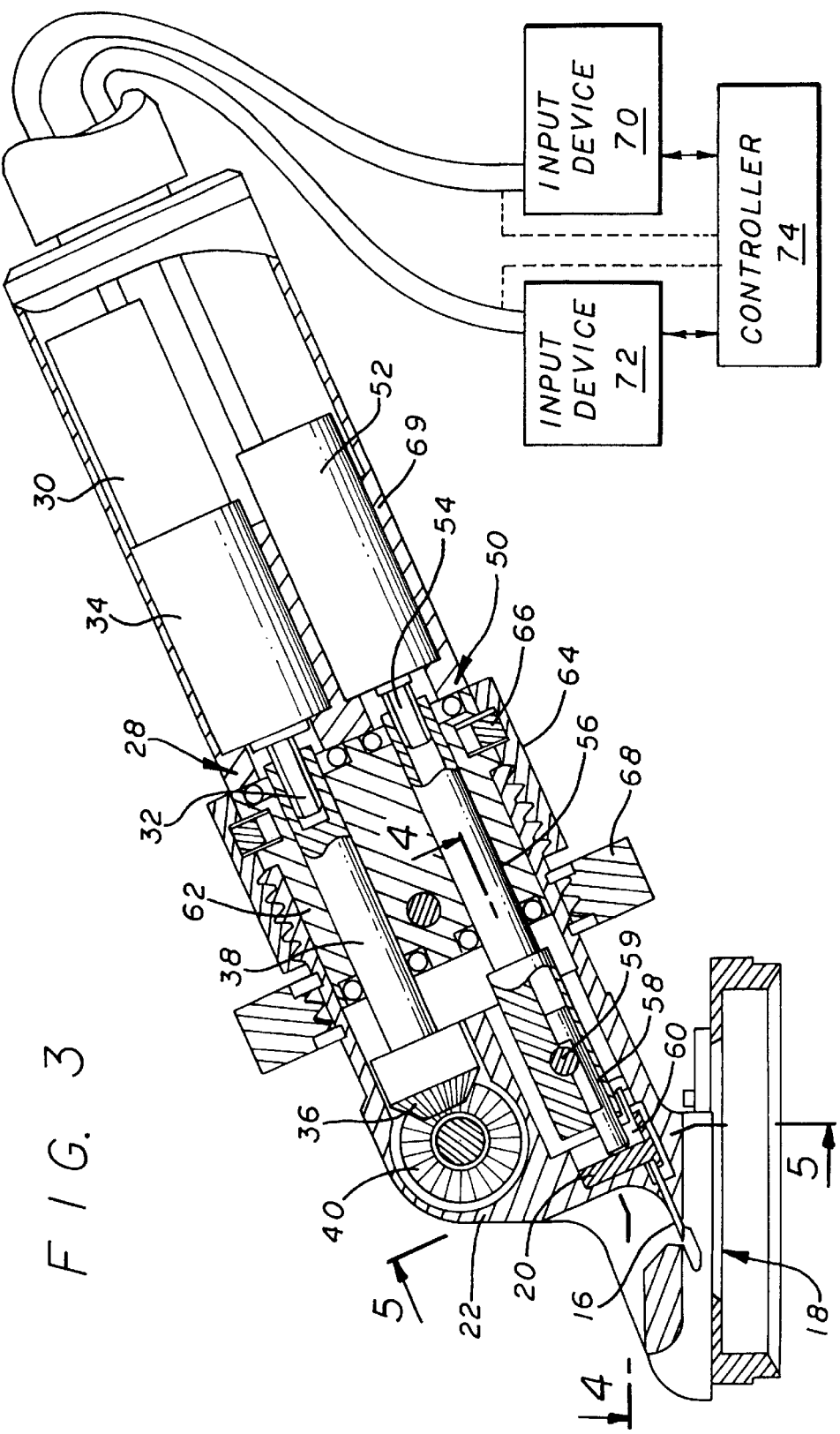
FIG. 3 is a cross-sectional view taken at line 3—3 of FIG. 2.

Referring to FIGS. 2 and 3, the device 10 includes a first drive mechanism 28 which moves the head 22, the blade holder 20 and the blade 16 in the first direction. The first drive mechanism 28 may include a first motor 30 that is coupled to an output shaft 32 by a gear reduction box 34. By way of example, the motor 30 may be an electric motor. The motor 30 may be coupled to a first gear 36 by a shaft 38 that is attached to the output shaft 32.

The first gear 36 may be coupled to a second gear 40 that is mounted to the head 22. The second gear 40 may be connected to a third gear 42 by a shaft 44. The third gear 42 may be coupled to a gear rack 46 (see also FIG. 1). The first 36 and second 40 gears may be of the bevel type so that rotation of the motor output shaft 32 imparts a corresponding rotation of shaft 44 and third gear 42. Rotation of the third gear 42 along the gear rack 46 causes the head 22, blade holder 20 and blade 16 to move in the first direction.

As shown in FIG. 1, the gear rack 46 may be located on a pedestal 48 that is attached to the ring 12. The pedestal 48 elevates the rack 46 above the cornea so that there is a low probability of an eye lash becoming stuck in the rack and pinion gear assembly.

Figure 4:
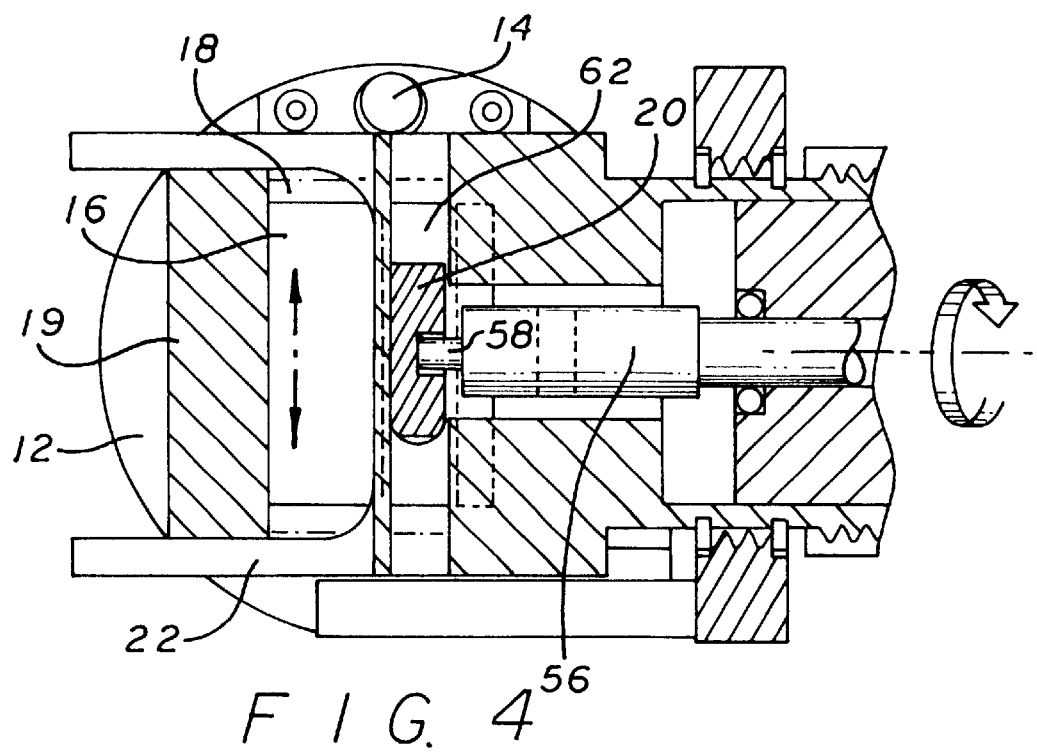
FIG. 4 is a cross-sectional view taken at line 4—4 of FIG. 3.

Referring to FIGS. 3–5, the device 10 may also have a second drive mechanism 50 that moves the blade holder 20 and the blade 16 in the second direction. The second drive mechanism 50 may include a second motor 52 which has an output shaft 54. By way of example, the motor 52 may be an electric motor. The output shaft 54 may be attached to a shaft 56 which has an eccentric cam pin 58. The cam pin 58 may be captured within the shaft 54 by another pin 59. The eccentric cam pin 58 fits within a slot 60 of the blade holder 20.

Rotation of the motor output shaft 54 moves the pin 58 about the center axis of the shaft 56. The eccentric rotation of the pin 58 moves the blade holder 20 and blade 22 within a slot 62 of the head 22 in the second direction. The pin 58 slides along the blade holder slot 60 in a vertical direction so that the blade 16 does not move into and out of the cornea.

The output shafts 38 and 56 may extend through a bulkhead 62 that is partially located within the head 22. A collar 64 and clip 66 attach the bulkhead 62 to the head 22. The device 10 may further have a lacking ring 68 for the collar 64. The motors 30 and 52 may be housed within a motor casing 69.

The first motor 30 may be connected to a first input device 70. The second motor 52 may be connected to a second input device 72. By way of example, the input devices 70 and 72 may be foot pedals which can be operated by a surgeon to control the actuation and speed of the motors 30 and 52. This allows the surgeon to separately control the movement of the blade 16 in the first direction and the movement of the blade 16 in the second direction. The surgeon can thus vary the shape and size of the cut.

The device 10 may further include a controller 74 which can be programmed to control the first 28 and second 50 drive mechanisms. The controller 74 can be used in conjunction with the input devices 70 and 72. The controller 74 may have programmable limit functions which limit the speed of the motors 30 and 52.

Figure 6:
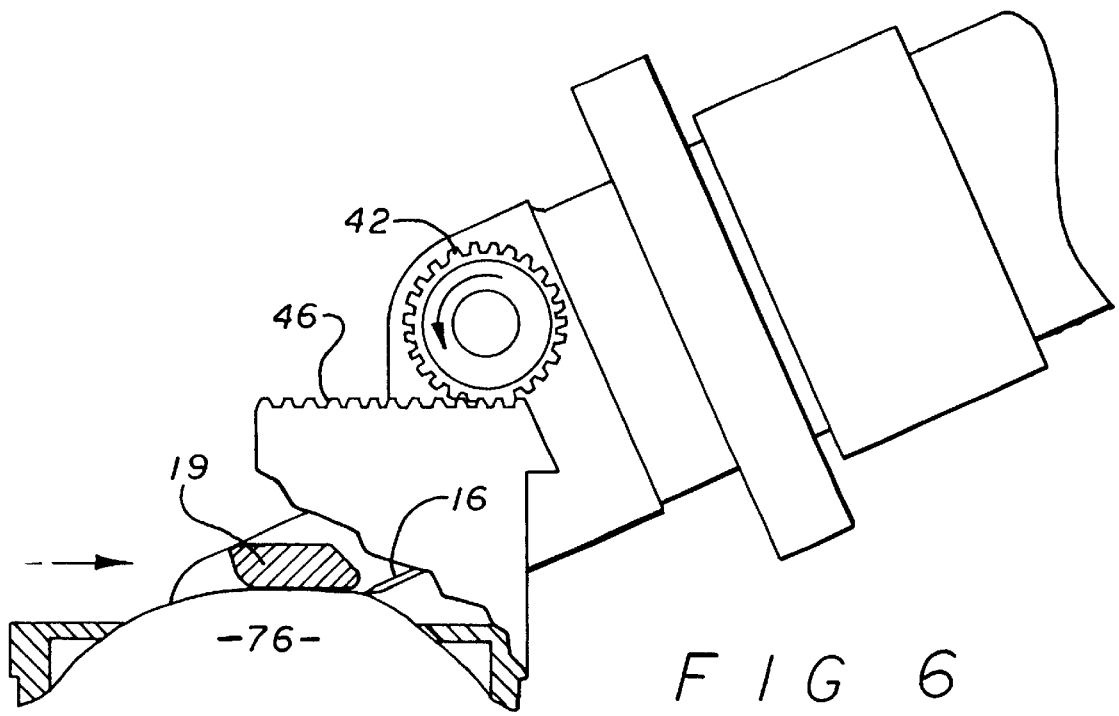
FIG. 6 is a side sectional view showing the device placed on a cornea.
Figure 7:
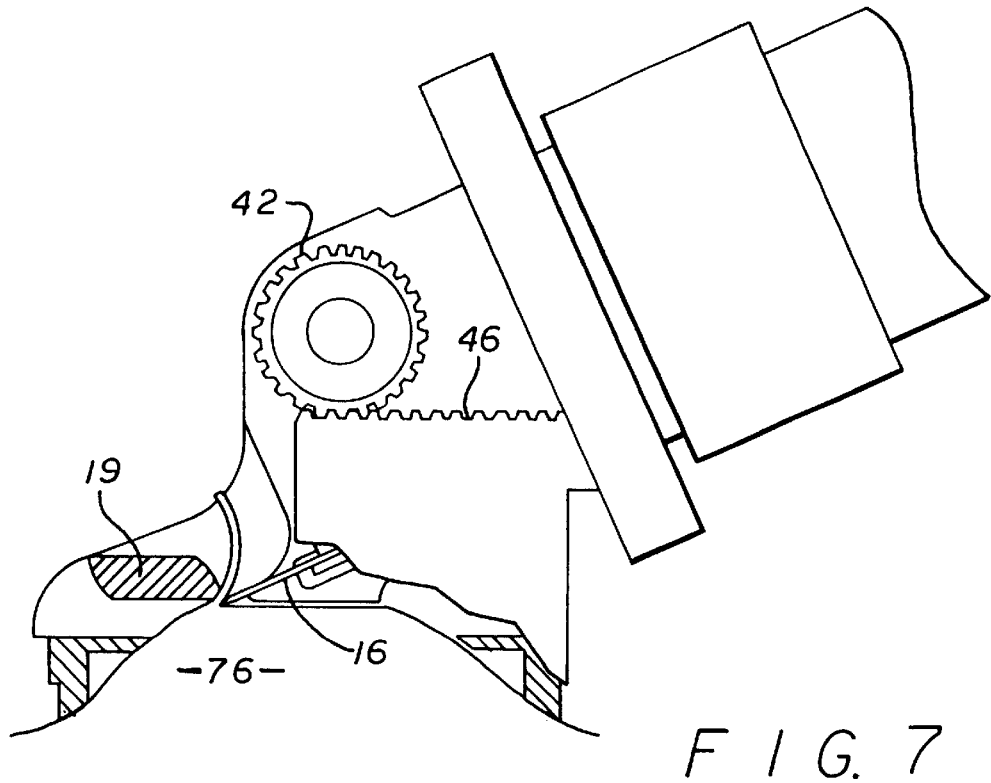
FIG. 7 is a side sectional view showing the device cutting the cornea.

As shown in FIGS. 6 and 7, in operation the ring 12 is placed on a cornea 76. The plate 19 tends to flatten the cornea 76 adjacent to the blade 16. The surgeon actuates the first 28 and second 50 drive mechanisms to move the blade 16 in the first and second directions. The movement of the blade cuts the cornea 76.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical device for cutting a cornea, comprising:
   a ring which has an opening;
   a blade that is located within said ring opening;
   a first drive mechanism that includes a first motor and moves said blade in a first direction; and,
   a second drive mechanism that includes a second motor and moves said blade in a second direction.

2. The device as recited in claim 1, further comprising a blade holder that holds said blade and which can move relative to said ring, and a head that supports said blade holder and which can move relative to said ring.

3. The device as recited in claim 2, wherein said first drive mechanism includes a first gear that is coupled to said first motor, a second gear that is coupled to said first gear, a third gear that is coupled to said second gear and a rack that mates with said third gear.

4. The device as recited in claim 3, wherein said first drive mechanism further includes a gear reduction box coupled to said motor and said first gear.

5. The device as recited in claim 3, wherein said rack is located on a pedestal that extends from said ring.

6. The device as recited in claim 1, wherein said second motor that rotates an eccentric pin which moves said blade in the second direction.

7. The device as recited in claim 1, wherein the second direction is essentially perpendicular to the first direction.

8. The device as recited in claim 1, further comprising a first input device to control said first drive mechanism and a second input device to control said second drive mechanism.

9. A medical device for cutting a cornea, comprising:
   a ring which has an opening;
   a blade that has a cutting edge located within said ring opening;
   a pedestal which extends from said ring, said pedestal having a rack that is located above said cutting edge away from said ring opening;
   a first drive mechanism which cooperates with said rack to move said blade in a first direction; and,
   a second drive mechanism which moves said blade in a second direction.

10. The device as recited in claim 9, further comprising a blade holder that holds said blade and which can move relative to said ring, and a head that supports said blade holder and which can move relative to said ring.

11. The device as recited in claim 10, wherein said first drive mechanism includes a motor, a first gear that is coupled to said motor, a second gear that is coupled to said first gear, a third gear that is coupled to said second gear and said rack.

12. The device as recited in claim 11, wherein said first drive mechanism further includes a gear reduction box coupled to said motor and said first gear.

13. The device as recited in claim 9, wherein said second drive mechanism includes a motor that rotates an eccentric pin which moves said blade in the second direction.

14. The device as recited in claim 9, wherein the second direction is essentially perpendicular to the first direction.

15. The device as recited in claim 9, further comprising a first input device to control said first drive mechanism and a second input device to control said second drive mechanism.

* * * * *

UNITED STATES PATENT AND TRADEMARK OFFICE
CERTIFICATE OF CORRECTION

PATENT NO. : 6,358,260 B1
DATED : March 19, 2002
INVENTOR(S) : Rod Ross and Greggory Hughes It is certified that error appears in the above-identified patent and that said Letters Patent is hereby corrected as shown below:

<u>Title page,</u>
"15 Claims" should read -- 7 Claims --

<u>Column 4,</u>
Lines 1-63, please replace with:

--What is claimed is:
1. A medical device for cutting a cornea, comprising:
a ring which has an opening and a top surface;
a handle coupled to said ring at an oblique angle relative to said top surface;
a blade that is located within said ring opening;
a first drive mechanism that includes a first motor and moves said blade in a first direction, said first motor being located within said handle; and,
a second drive mechanism that includes a second motor and moves said blade in a second direction, said second motor being located within said handle.
2. The device as recited in claim 1, further comprising a blade holder that holds said blade and which can move relative to said ring, and a head that supports said blade holder and which can move relative to said ring.
3. The device as recited in claim 2, wherein said first drive mechanism includes a first gear that is coupled to said first motor, a second gear that is coupled to said first gear, a third gear that is coupled to said second gear and a rack that mates with said third gear.
4. The device as recited in claim 3, wherein said first drive mechanism further includes a gear reduction box coupled to said motor and said first gear.
5. The device as recited in claim 3, wherein said rack is located on a pedestal that extends from said ring.
6. The device as recited in claim 1, wherein said second motor rotates an eccentric pin which moves said blade in the second direction.
7. The device as recited in claim 1, wherein the second direction is essentially perpendicular to the first direction.--

Signed and Sealed this

Twenty-seventh Day of May, 2003

JAMES E. ROGAN
*Director of the United States Patent and Trademark Office*